United States Patent

Biedermann et al.

[11] Patent Number: 5,989,290
[45] Date of Patent: Nov. 23, 1999

[54] HEIGHT-ADJUSTABLE ARTIFICIAL VERTEBRAL BODY

[76] Inventors: Lutz Biedermann, Am Schäferersteig 8, 78048 VS-Villingen; Jürgen Harms, Vogesenstrasse 60, 76337 Waldbronn, both of Germany

[21] Appl. No.: 08/952,908
[22] PCT Filed: May 15, 1996
[86] PCT No.: PCT/EP96/02092
§ 371 Date: Nov. 24, 1997
§ 102(e) Date: Nov. 24, 1997
[87] PCT Pub. No.: WO96/37170
PCT Pub. Date: Nov. 28, 1996

[30] Foreign Application Priority Data

May 24, 1995 [DE] Germany ............... 195 19 101

[51] Int. Cl.$^6$ ............... A61F 2/44; A61B 17/70
[52] U.S. Cl. ............... 623/17; 606/61
[58] Field of Search ............... 623/17; 606/61

[56] References Cited

U.S. PATENT DOCUMENTS

| 4,401,112 | 8/1983 | Rezaian | 623/17 X |
| 4,657,550 | 4/1987 | Daher | 623/17 |
| 5,458,641 | 10/1995 | Ramirez Jimenez | 623/17 |
| 5,571,192 | 11/1996 | Schonhoffer | 623/17 |
| 5,702,453 | 12/1997 | Rabbe et al. | 623/17 |

FOREIGN PATENT DOCUMENTS

| 0 392 076 | 10/1990 | European Pat. Off. |
| 30 23 942 | 1/1982 | Germany . |
| 91 07 494 U | 10/1991 | Germany . |
| 395 524 | 1/1993 | Germany . |
| 43 23 034 C1 | 7/1994 | Germany . |
| 43 15 757 C1 | 11/1994 | Germany | 623/17 |
| 44 09 392 A1 | 9/1995 | Germany . |
| 44 23 257 A1 | 1/1996 | Germany . |
| 5-15548 | 1/1993 | Japan | 623/17 |
| WO 96/17564 | 6/1996 | WIPO . |

*Primary Examiner*—David H. Willse
*Attorney, Agent, or Firm*—Dike, Bronstein, Roberts & Cushman, LLP; George W. Neuner

[57] ABSTRACT

A substitute vertebra with adjustable height is provided with a sleeve-shaped central part (1) having a wall with a plurality of apertures (5, 6), the central part comprising a left-handed thread adjacent to its first edge and a right-handed thread adjacent to its second edge. A cylindrical first part (7) is connected with the one threaded portion through a corresponding thread and a cylindrical second part (9) is connected to the other threaded portion through a corresponding thread. Both parts (7, 9) also have walls with a plurality of apertures (8). The two parts (7, 9) both have a plurality of teeth (8) provided at their free edges.

10 Claims, 2 Drawing Sheets

HEIGHT-ADJUSTABLE ARTIFICIAL VERTEBRAL BODY

The invention relates to a substitute vertebra with adjustable height.

The German utility model 91 07 494.0 discloses a substitute vertebra with adjustable height and a threaded rod which comprises a central portion for engagement of a wrench for rotating the rod, a contiguous portion having a left-handed thread and an opposite second portion having a right-handed thread. A respective support member having a corresponding thread is connected to each threaded portion. The support member has a free face with prongs projecting in a direction parallel to the axis. Other vertebrae implants with adjustable height are described in documents AT-B-395 524, U.S. Pat. No. 4,657,550 and DE-C-30 23 942.

It is the object of the invention to provide a substitute vertebra with adjustable height which is mechanically simple and easy to use, and which enhances the growth together.

This object is achieved by the substitute vertebra with adjustable height.

In accord with the present invention, a substitute vertebra with adjustable height has a sleeve-shaped central part (1) comprising a left-handed thread adjacent to a first edge thereof and a right-handed thread adjacent to a second edge thereof, a cylindrical first part (7) having a wall with a plurality of apertures (5, 6) and a cylindrical second part (9) having a wall with a plurality of apertures (5, 6), whereby the first part (7) has a thread cooperating with the right-handed thread, and whereby both cylindrical parts have a plurality of teeth (8) at a first edge provided at their free end. Other preferred embodiments are characterized in that (a) the thread of each of the cylindrical parts (7, 9) is provided at the second edge thereof opposite to the first edge, (b) the threads of the central part (10 are formed as an external thread and the threads of the cylindrical parts are formed as internal threads, (c) the central part (1) comprises a portion (5) provided between the threaded portions (3, 4) for rotating the central part (1) relative to parts (7, 9), (d) a device is provided for locking the central part (1) against rotation relative to at least one of the cylindrical parts (7, 8), (e) the apertures (5, 6) in the wall parts (7, 9) and in the central part are formed as quadrangles or diamonds (8) extending substantially in an axial direction of the hollow bodies, and (f) titanium sheet metal or titanium tube material is used.

Further features and advantages of the invention will be apparent from the description of embodiments with reference to the figures.

Figure 2:
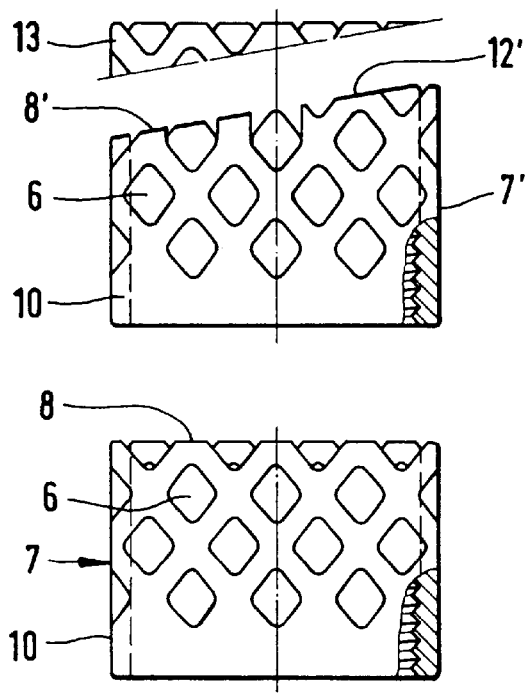
FIG. 2 shows a treated detail of FIG. 1.

The substitute vertebra with adjustable height has a cylindrical central part 1. The central part comprises a raised ring 2 in the middle along the axial direction of the central part and threaded portions 3 and 4 at the adjacent portions on both sides. One of the portions 3 is formed as a left-handed thread and the other portion 4 is formed as a right-handed thread. The ring 2 has peripherally distributed bores 5 and the threaded portions 3 and 4 have coaxially aligned rhombic apertures 6.

Figure 1:
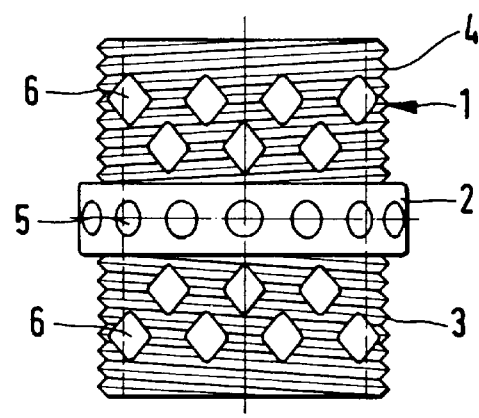
FIG. 1 is a side view of a first embodiment in exploded representation.
Figure 1:
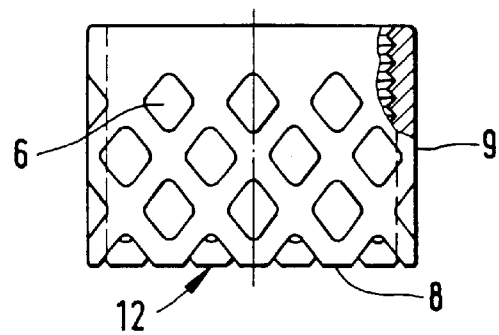

There is further a cylindrical first part 7 which comprises a thread cooperating with the thread of the threaded portion 4 on its inner side. In operation the first part 7 is screwed onto the threaded portion 4. The wall is formed of a material having rhombic apertures 6 provided at circumferentially and axially offset positions. A plurality of circumferentially spaced teeth are formed at the free end of the first part facing away from the ring 2. As shown in FIG. 1 the teeth are formed by positioning the edge in circumferential direction along the center line of a row of rhombs 6.

The second part 9 differs from the first part only in that its interior thread is formed to cooperate with the thread of the threaded portion 3. In operation the second part is screwed onto the threaded portion 3.

Preferably, the rhombic apertures 6 in the two threaded portions 3 and 4 have the same size and spacial arrangement as the rhombs of the first and second part. The outer diameter of the ring 2 is substantially equal to the outer diameter of the first and second part 7, 9, respectively.

Preferably, the material for the substitute is titanium sheet metal or titanium tube, respectively; in any case it should be a biocompatible material.

Figure 4A:
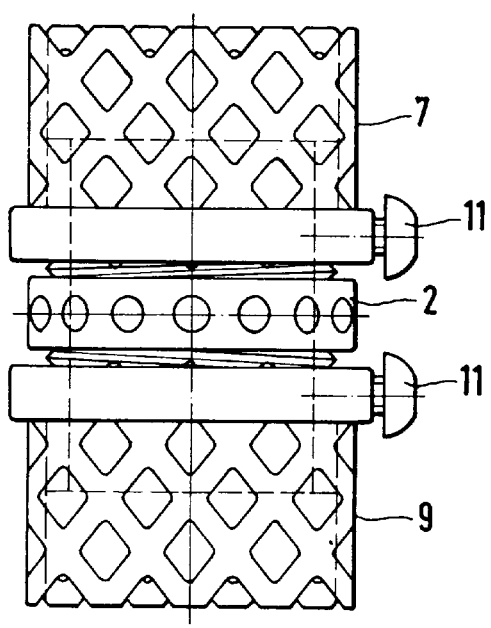
FIGS. 4a and 4b are side views of an embodiment in two different adjustment positions.
Figure 4B:
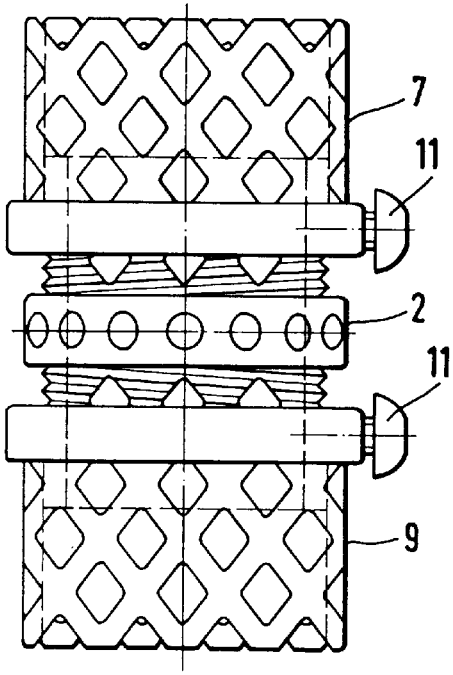

In operation the described substitute vertebra is simply placed, while being screwed together, between the parts to be supported and the height thereof is adjusted by rotating the ring 2. According to FIG. 4a the substitute vertebra is nearly completely screwed together into the starting position having a minimum height, whereas in the position shown in FIG. 4b the height is increased by unscrewing. The engagement with the adjacent parts is secured against rotation by the teeth 8.

Bone substance to be introduced to the interior of the hollow substitute vertebra can easily grow through the apertures 5 and 6.

Figure 3:
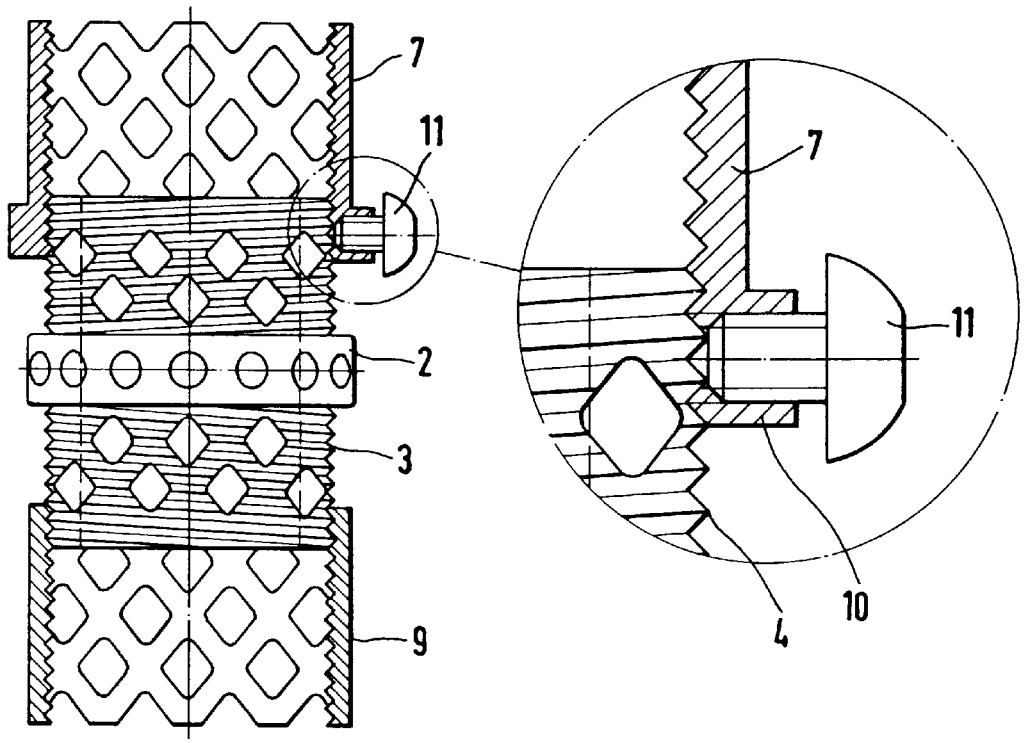
FIG. 3 shows a modified embodiment in partially sectional representation.

FIG. 3 shows an embodiment of a thread rotation lock for the above-described substitute vertebra. A capscrew or grub-screw 11 is mounted in radial direction at the end 10 of the first part 7 facing the ring 2 in such a manner that it engages, in the manner shown in FIG. 3, the thread of the corresponding threaded portion of the central part and effects a lock thereat. As shown in FIG. 3 the grubscrew is conducted by a thread provided within the jacket of the first part.

As best shown in FIG. 2 the design of the jacket of each of the parts 7, 7', 9 makes it possible to easily adapt the inclination of the end surfaces 12 to be brought into engagement with the adjacent vertebra by severing, using suitable sheet shears, a portion 13 corresponding to the desired inclination to thereby produce an inclined engagement surface 12'. Owing to the choice of the material the new engagement surface 12' also comprises corresponding teeth 8'.

In operation the screws 11 are locked after adjusting the height by rotating the central part 1 through the ring 2 to thereby achieve a stable lock which is secured against unscrewing by itself.

We claim:

1. An adjustable substitute vertebra comprising:
   a sleeve-shaped central member having a first end, a second end, a left-handed thread provided on said central member adjacent said first end and a right-handed thread provided on said central member adjacent said second end,
   a cylindrical first member having a wall, a plurality of apertures provided in said wall, a thread for screwing said first member onto said left-handed thread on said central member at one side thereof, the other side of said first member forming a free end which comprises a plurality of teeth,
   a cylindrical second member having a wall, a plurality of apertures provided in said wall, a thread for screwing said second member onto said right-handed thread on said central member at one side thereof, the other side of said second member forming a free end which comprises a plurality of teeth, said first and second member being made from titanium sheet material or titanium tube material, said cylindrical first member further comprising a plurality of V-shaped apertures at its free end to define said plurality of teeth, and said cylindrical second member further comprising a plurality of V-shaped apertures at its free end to define said plurality of teeth.

2. The substitute vertebra of claim 1, wherein said thread of each of said cylindrical first and second members is provided adjacent to a first edge thereof opposite to a second edge formed at said free end, thereof.

3. The substitute vertebra of claim 1, wherein the left-handed thread and right-handed thread provided on said central member is formed as external threads and the threads formed on said first and second member being formed as internal threads.

4. The substitute vertebra of claim 1, further comprising a portion for rotating said central member relative to said first and second member, said portion being provided on said central member between said left-handed thread and said right-handed thread.

5. The substitute vertebra of claim 1, further comprising means for locking said central member against rotation relative to at least one of said first and second members.

6. The substitute vertebra of claim 1, wherein said apertures in said walls of said first and second members are formed as quadrangles or as diamonds extending substantially in an axial direction of said first and second members, respectively.

7. The substitute vertebra of claim 1, wherein said central member, first member and second member are made of titanium sheet material.

8. The substitute vertebra of claim 1, wherein said central member, said first member and said second member are formed of titanium tube material.

9. The substitute vertebra of claim 1, wherein said central member comprises a wall containing apertures formed as quadrangles or as diamonds extending substantially in axial an direction of the central member.

10. The substitute vertebra of claim 9, wherein said apertures in said walls of said first and second members are formed as quadrangles or as diamonds extending substantially in axial an direction of said first and second members, respectively.

* * * * *